United States Patent [19]

Ross

[11] Patent Number: 4,862,172
[45] Date of Patent: Aug. 29, 1989

[54] COMPUTER CONTROL APPARATUS INCLUDING A GRAVITY REFERENCED INCLINOMETER

[75] Inventor: J. David Ross, DeSoto, Tex.

[73] Assignee: Texas Scottish Rite Hospital for Crippled Children, Dallas, Tex.

[21] Appl. No.: 96,973

[22] Filed: Sep. 14, 1987

[51] Int. Cl.$^4$ .............................................. H03M 1/60
[52] U.S. Cl. ................................... 341/157; 340/709; 341/13
[58] Field of Search ............... 340/696, 345, 706, 709, 340/710, 711; 364/709; 341/126, 157, 158, 13, 155; 33/366

[56] References Cited

U.S. PATENT DOCUMENTS

| | | | |
|---|---|---|---|
| 3,541,541 | 11/1970 | Engelbart | 340/710 |
| 3,689,840 | 9/1972 | Brown et al. | 375/27 |
| 4,468,864 | 9/1984 | Westphal et al. | 33/366 |

OTHER PUBLICATIONS

Bailey et al., Shaft Position and Direction Encoder, IBM Technical Disclosure Bulletin, vol. 14, No. 1, 6/1971, pp. 54 & 55.
The Engineering Staff of Analog Devices, Inc., Analog-Digital Conversion Handbook, 6/1972, p. III-4.

Primary Examiner—William M. Shoop, Jr.
Assistant Examiner—Brian K. Young
Attorney, Agent, or Firm—Harry C. Post, III

[57] ABSTRACT

Computer control apparatus uses sensing apparatus converts a mechanical movement into a direct current electrical signal. An electrical interface circuit is connected to the sensing apparatus for converting the direct current electrical signal into a pulse output used in controlling a computer. The preferred sensor is an inclinometer, which comprises an opaque body having a chamber. A light source is connected to the body to provide light in the chamber. Photocell apparatus is connected to the body to receive light emitted from the light source for providing an electrical resistance in relation to the amount of light received. Supported in the chamber is a liquid filter medium to absorb light emitted from the light source. A sufficient quantity of liquid filter medium is provided in the chamber to prevent light emitted from the light source from impinging upon the photocell apparatus in response to the angular placement of the body with respect to gravity.

21 Claims, 7 Drawing Sheets

COMPUTER CONTROL APPARATUS INCLUDING A GRAVITY REFERENCED INCLINOMETER

It is well known that a personal computer may be used by a person for work or play by providing access to immense stores of knowledge, to games, to bookkeeping, to word processing and the like. Normally the computer is controlled by a person manipulating a keyboard, a switch, a potentiometer, a joystick and the like. Because the control of the computer requires the use of a person's arms or hands, a person unable to use his hands or arms is prevented from using the computer.

To enable such a handicapped person to control a computer, it was decided to develop an inclinometer connected to the head of the person so that angular displacement of the inclinometer relative to gravity is converted into an electrical signal. Although gravity referenced inclinometers, such as the bubble vial in a carpenter's level or a tilt gauge, have been known for some time, it is necessary for computer control apparatus to have an electrical signal output proportional to the pitch of the sensor. This latter type of sensor is used extensively in scientific, industrial and military applications where it is necessary to monitor from a remote location or to interface with a computer, but such prior art sensors are bulky or too expensive for such in computer control apparatus.

To enable the conversion of the electrical signal from the inclinometer into a computer control signal, it was decided to develop an electrical interface circuit to convert the direct current electrical signal into a pulse output used in controlling a computer capable of using a mouse. Since the pulse output is used in controlling a computer capable of using a mouse, any sensor converting a mechanism input into a direct current electrical signal that is proportionate to the input may be used with the electrical interface circuit.

Accordingly, it is an object of the present invention to provide computer control apparatus that will permit a person unable to use his hands or arms to operate a computer.

Another object of the present invention is to provide computer control apparatus, which includes a gravity referenced inclinometer connected to the person, so that a person unable to use his hands or arms can operate the computer.

Another object of the present invention is to provide an inclinometer that converts an angular displacement of the inclinometer relative to gravity into an electrical signal.

Another object of the present invention is to provide an electrical interface circuit that converts the direct current electrical signal from a sensor into a pulse output used in controlling a computer.

In accordance with the invention, there is provided computer control apparatus, comprising: sensing apparatus and an electrical interface circuit. The sensing apparatus converts a mechanical movement into a direct current electrical signal. The electrical interface circuit is connected to the sensing apparatus for converting the direct current electrical signal into a pulse output used in controlling a computer.

Further, in accordance with the invention, there is provided an inclinometer, which comprises an opaque body having a chamber. A light source is connected to the body to provide light in the chamber. A photocell is connected to the body to receive light emitted from the source for providing an electrical resistance in relation to the amount of light received. A liquid filter medium is supported in the chamber to absorb light emitted from said light source. There is a sufficient quantity of liquid filter medium provided in the chamber to prevent light emitted from the light source from impinging upon the photocell in response to the angular placement of the body relative to gravity.

Other objects and advantages of the invention will become apparent upon reading the following detailed description and upon reference to the drawings, wherein like reference characters are used throughout to designate the like parts:

Figure 1:
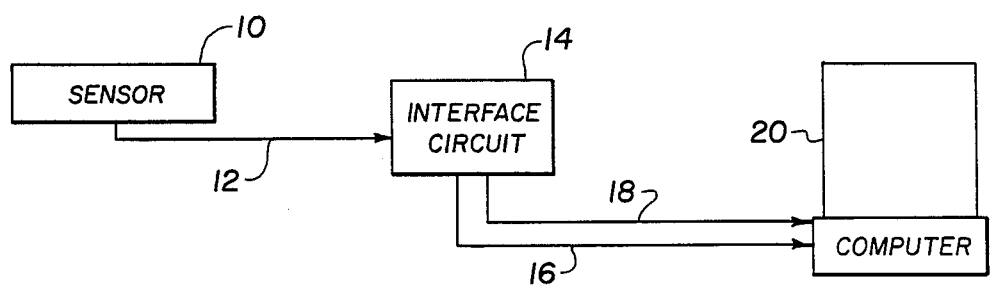
FIG. 1 is a schematic drawing of computer control apparatus constructed according to the present invention.

Turning to FIG. 1, there is shown a sensing apparatus 10 connected by conductor 12 to an interface circuit 14, which is connected by conductors 16 and 18 to a computer 20 of conventional construction having an input for a mouse, such as Apple Computer IIE.

Figure 2:
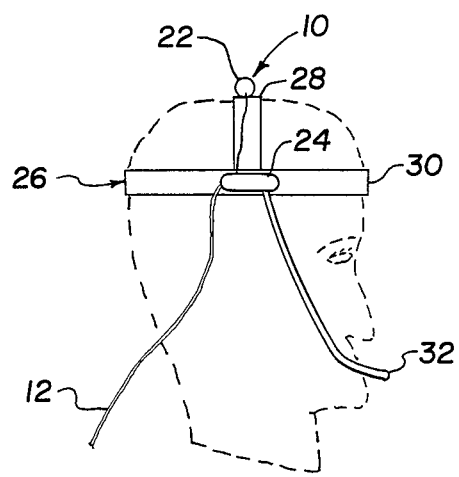
FIG. 2 is a side elevational view of a sensing portion of the apparatus constructed according to the present invention and connected to the head of a person controlling a computer.

As best seen in FIGS. 1 and 2, sensing apparatus 10 includes first and second inclinometer 22 and 24, respectively, which are connected to the head of a person (shown in dotted outline) by a harness 26. First inclinometer 22 is connected to an over-the-head strap 28 of harness 26 so that tilting the head to the left or right provides a horizontal movement of a cursor on the display screen of computer 20 along an X-axis (left to right of the screen). Second inclinometer 24 is connected to an around-the-head strap 30 of harness 26 so that nodding the head to the front or back will provide a vertical movement of the cursor on the display screen of computer 20 along the Y-axis (top to bottom of the screen). A microphone 32 may be connected to harness 26 so that a voice activated switch is selectively activated and deactivated to operate the program when the cursor is properly positioned on the screen. The electrical signals from inclinometers 22 and 24 and microphone 32 are carried through conductor 12 into interface circuit 14.

Figure 3:
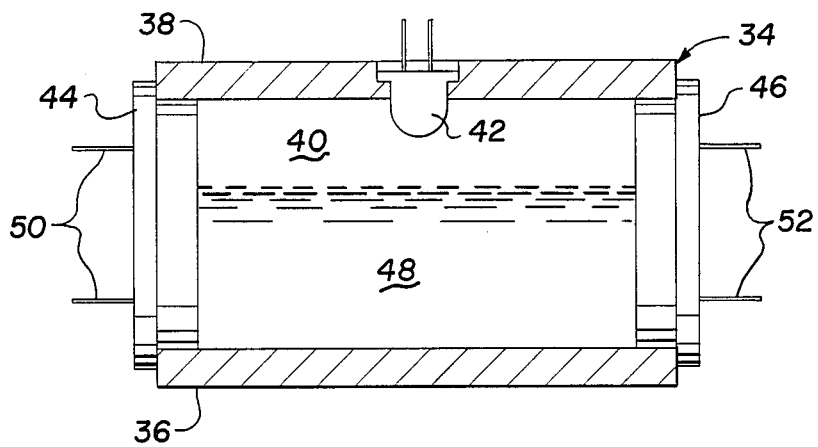
FIG. 3 is a side elevation view of a gravity referenced inclinometer used in the sensing portion shown in FIG. 2.

As seen in FIG. 3, a preferred inclinometer 34 is shown, which may be used for both inclinometers 22 and 24. Inclinometer 34 has an opaque body 36 that is constructed from a tube 38 with the channel in the tube forming a chamber 40.

To provide light in chamber 40, a light source 42 is connected to body 36 midway between each end of tube 38. Preferably, light source 42 is a light emitting diode, such as that sold with the model No. AND124R, which has a single peak optical coupling at a wavelength of 700 nm.

A photocell apparatus is connected to body 36 to receive light emitted from light source 42 for providing an electrical resistance in relation to the amount of light received from light source 42. To provide the electrical resistance in relation to the amount of light received from light source 42, a first photoconductive cell 44 is disposed in one end of tube 38 and connected to body 36 and a second photoconductive cell 46 is disposed in the other end of tube 38 and connected to body 36. Photocells 44 and 46 are conventional light dependent resistors similar to those used in photographic light meters, such as those sold with model No. VT54L.

A liquid filter medium 48 to absorb light emitted from light source 42 is supported within chamber 40. A sufficient quantity of liquid filter medium 48 is provided in chamber 40 to prevent light emitted from light source 42 from impinging upon photocells 44 and 46 in response to the angular movement of body 36 with respect to gravity. It is preferred that the amount of liquid filter medium 48 provided within chamber 40 is sufficient to fill body 36 approximately one-half full. Filter medium 48 is chosen to provide vibration dampening and is preferably a mixture of an SAE-30 weight oil diluted 3:1 with mineral spirits to provide an acceptable balance between light opacity and dampening and a dye having a color chosen to absorb the single peak optical coupling of light emitting diode 42, such as a green dye when using a light emitting diode in the 700 nm range. As inclinometer 34 is tilted along its active axis (the axis extending concentrically with tube 38), filter medium 48 differentially regulates the amount of light allowed to strike each photocells 44 and 46.

The range of inclinometer 34 is determined by the spacing between photocells 44 and 46. That is, an inclinometer 34 that is used in measuring large pitch angles will have a body length shorter than the body length of an inclinometer 34 used in measuring small pitch angles.

By connecting photocells 44 and 46 to body 36 at opposite ends of tube 38, this opposed configuration produces a linear output. Since both photocells 44 and 46 contribute to the signal output through conductor 12, the amplitude is double that produced by a single photocell. This complimentary action cancels out non-linearities in the transfer function of photocells 44 and 46 and increases the voltage swing of the output through conductors 50 and 52 running from photocells 44 and 46, respectively.

As best seen in FIG. 1 and 4-9, an interface circuit 54 is connected to each inclinometer 56 provided in the computer control apparatus. Each electrical interface circuit 54 converts direct current electrical signal from the connected inclinometer 56 into a pulse output transmitted through conductors 58 into conductor 16 or 18 to control computer 20.

Figure 9:
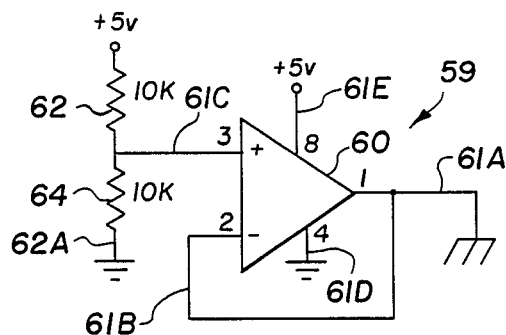
FIG. 9 is a schematic drawing of a portion of the electrical interface circuit shown in FIG. 4.

As best seen in FIGS. 1 and 9, a virtual ground circuit 59 is included in interface circuit 54 to provide symmetrical plus and minus power from a power source supplied through the mouse port of computer 20. Virtual ground circuit 59 includes an operation amplifier 60, a first resistor 62 and a second resistor 64. Operational amplifier 60 is of a conventional design, such as the operational amplifier/buffer sold by National Semiconductor under no. LM358, which has connecting point 1 connected to conductor 61A, connecting point 2 connected to conductor 61B, connecting point 3 connected to conductor 61C, connecting point 4 connected to conductor 61D and connecting point 8 connected to conductor 61E. Conductor 61A runs to other portions of the interface circuit, which is constructed according to the present invention. Conductor 61B runs to conductor 61A prior to connecting with the other portions of the interface circuit. Conductor 61C runs to and connects with a conductor 62A. Conductor 61D runs to ground and conductor 61E receives +5 volts of dc power provided by the mouse port of computer 20. Resistors 62 and 64 are provided within conductor 62A, which has one end receiving the +5 volts of dc power provided by the mouse port of computer 20 and the other end running to ground.

Figure 4:
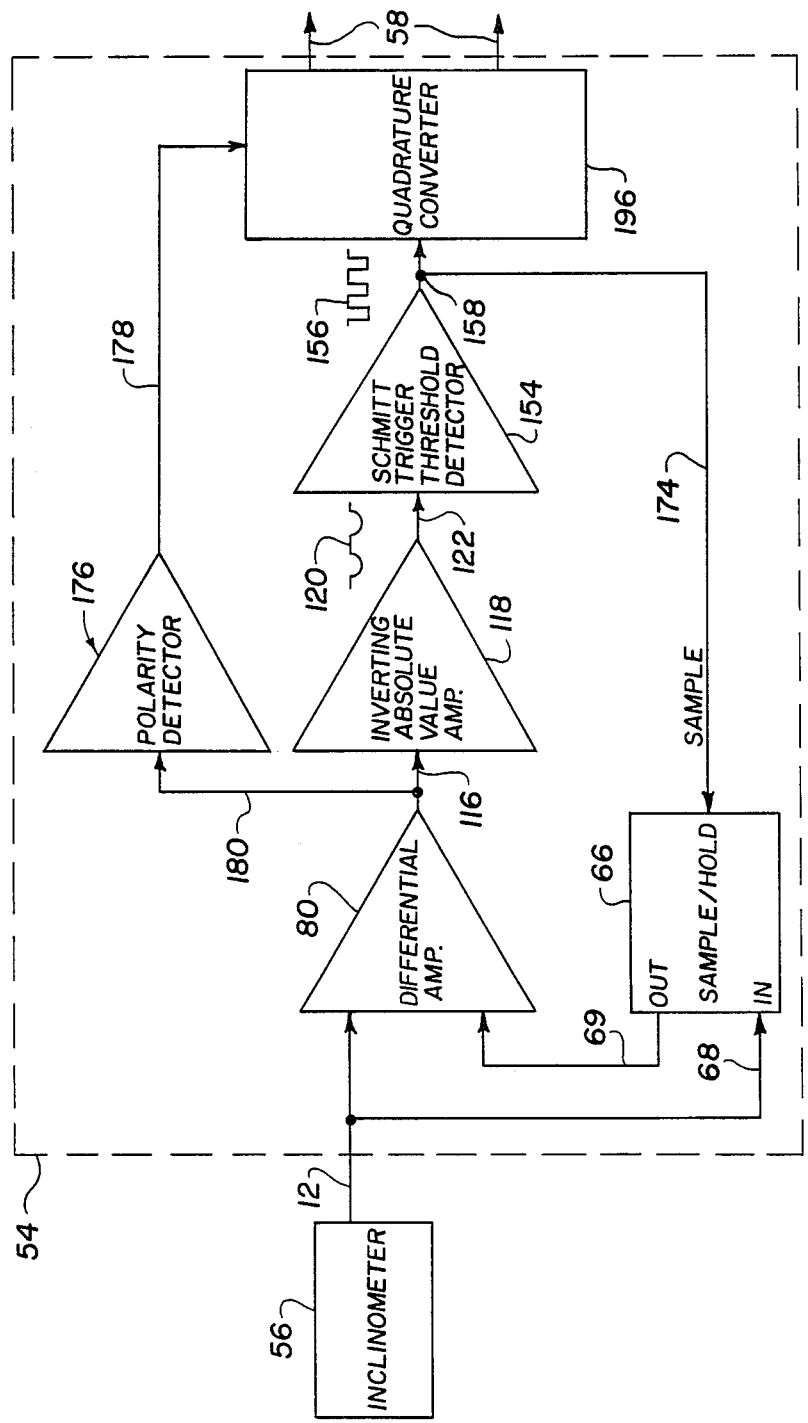
FIG. 4 is a schematic drawing of an electrical interface circuit constructed according to the present invention.
Figure 5:
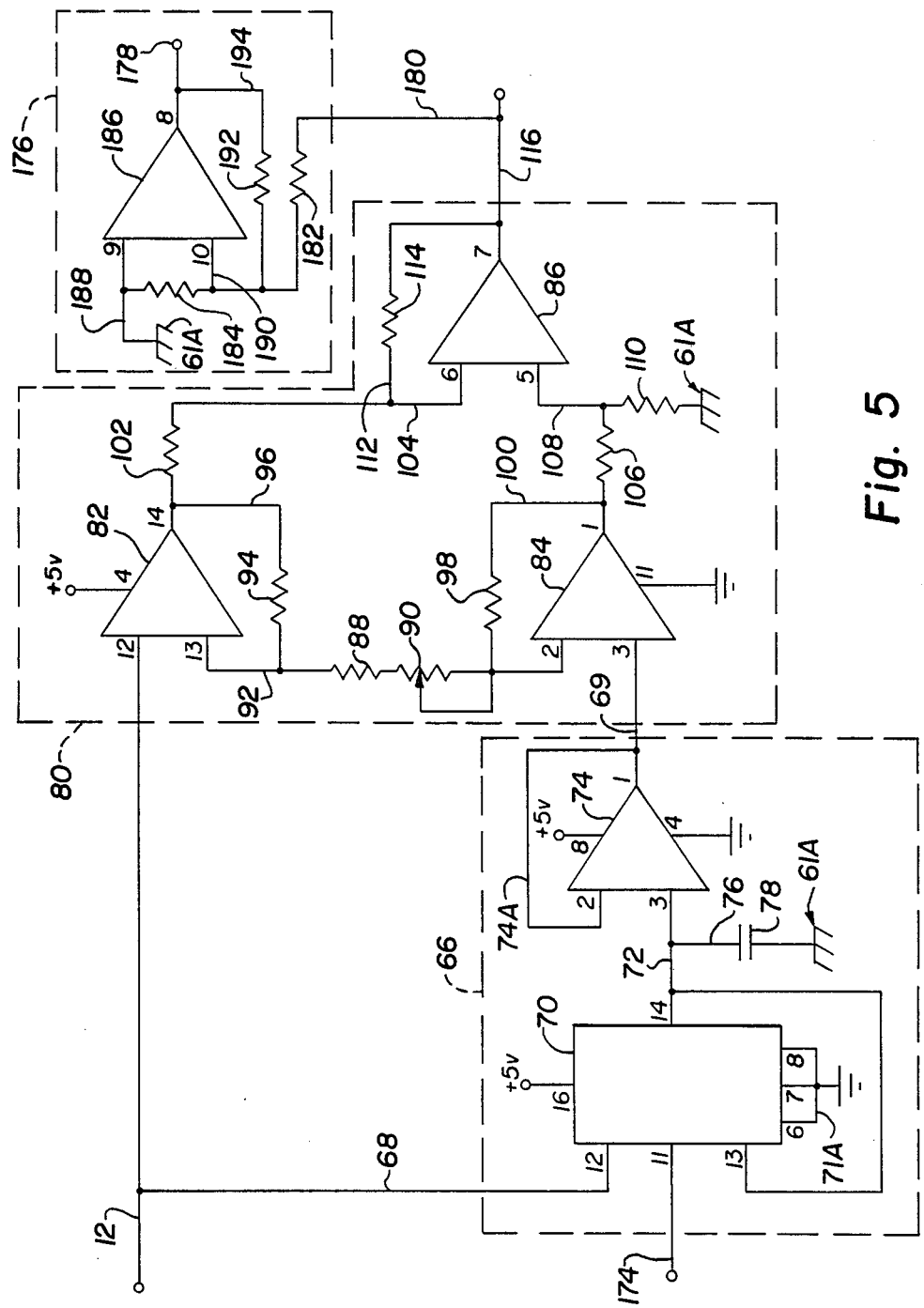
FIG. 5 is a schematic drawing of a portion of the electrical interface circuit shown in FIG. 4.

As best seen in FIGS. 4 and 5, a sample and hold circuit 66 provides a reference signal through a conductor 69 and is connected by conductors 12 and 68 to inclinometer 56. Sample and hold circuit 66 includes a 1-of-2 switch 70 and a dual operational amplifier 74 connected by conductor 72 to switch 70 and by conductors 72 and 76 to a capacitor 78, which is connected by a conductor to virtual ground circuit 59. Switch 70 is of conventional design, such as that sold in a package as triple 1-of-2 switch under the no. 4053, with connecting points 6, 7 and 8 connected by conductor 71A and running to ground, connecting point 1 connected to a conductor 174, connecting point 12 connected to conductor 12, connecting point 13 connected to conductor 71B and running to conductor 72, connecting point 14 connected to conductor 72, connecting point 16 connected to a conductor that receives the +5 volt dc power provided by the mouse port of computer 20. Dual operational amplifier 74 is of conventional design, such as that sold by Archer under no. TLC272, which has connecting point 1 connected to conductor 69, connecting point 2 connected to a conductor 74A running to conductor 69, connecting point 3 connected to conductor 72, connecting point 4 running to ground, and connecting point 8 connected to a conductor that receives the +5 volt dc power provided by the mouse port of computer 20. Capacitor 78 is of conventional design having a capacity of 0.01 microfarads.

A differential amplifier circuit 80 for providing a proportional electrical signal, which is an electrical signal that is an amplification of the difference in the voltages between the direct current electrical signal and the reference signal, is connected to inclinometer 56 by conductor 12 and to sample and hold circuit 66 by conductor 69. Differential amplifier circuit 80 includes three independent, high gain, internally frequency compensated operational amplifier/buffer 82, 84 and 86. Operational amplifier/buffers 82, 84 and 86 are of conventional design, such as that sold in a package by National Semiconductor under no. LM324, with these connecting points being indicated on the drawing. The +5 volt dc power provided by the mouse port of computer 20 at connecting point 4 into operational amplifier/buffer 82. A 10K fixed resistor 88 and a 50K variable resistor 90 are connected in series between connecting point 13 of operational amplifier/buffer 82 and connecting point 2 of operational amplifier/buffer 84 by conductor 92. A 100K fixed resistor 94 is connected between connecting points 13 and 14 of operational amplifier/buffer 82 by a conductor 96. A 100K fixed resistor 98 is connected to the wiper blade of variable resistor 90 and between connecting points 2 and 1 of operational amplifier/buffer 84 by a conductor 100. A 100K fixed resistor 102 is connected between connecting point 14 of operational amplifier/buffer 82 and connecting point 6 of operational amplifier/buffer 86 by a conductor 104. A 100K fixed resistor 106 is connected between connecting point 1 of operational amplifier/buffer 84 and connecting point 5 of operational amplifier/buffer 86 by a conductor 108. Connected to conductor 108 between fixed resistor 106 and connecting point 5 of operational amplifier/buffer 86 is a 100K fixed resistor 110, which is connected by a conductor to virtual ground circuit 59. At a point between fixed resistor 102 and connecting point 6 of operational amplifier/buffer 86, a conductor 112 is connected to conductor 104, which runs to a 100K fixed resistor 114 and a conductor 116 running from connecting point 7 of operational amplifier/buffer 86.

Figure 6:
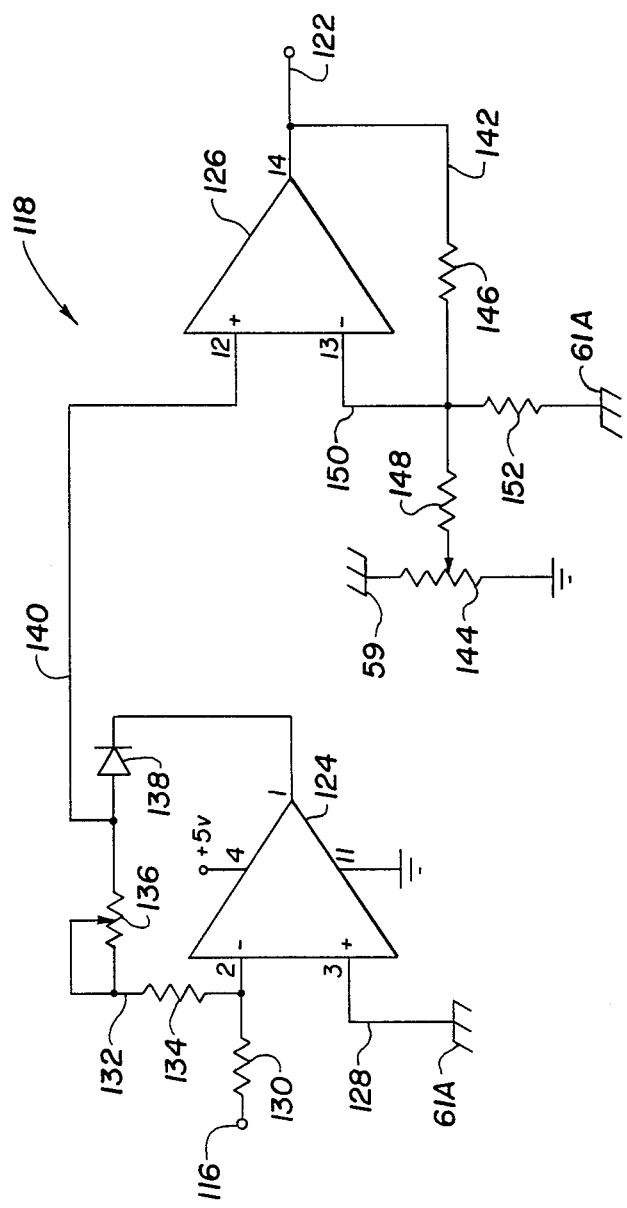
FIG. 6 is a schematic drawing of a portion of the electrical interface circuit shown in FIG. 4.

As best seen in FIGS. 4 and 6, an inverting absolute value amplifier circuit 118 for providing a negative going output signal 120 through a conductor 122 is connected to differential amplifier circuit 80 by conductor 116. Inverting absolute value amplifier circuit 118 includes includes two independent, high gain, internally frequency compensated operational amplifier/buffers 124 and 126. Operational amplifier/buffers 124 and 126 are of conventional design, such as that sold by National Semiconductor under no. LM324, with its connecting points being indicated on the drawing. Operational amplifier/buffer 124 is operated off of the +5 volt dc power provided by the mouse port of computer 20 at connecting point 4. A conductor 128 connects virtual ground circuit 59 to connecting point 3 of operational amplifier/buffer 124. A conventional 10K fixed resistor 130 is provided in conductor 116, which is connected to connecting point 2 of operational amplifier/buffer 124. A conductor 132 runs from a point between resistor 130 and connecting point 2 of operational amplifier/buffer 124 to connecting point 1 of operational amplifier/buffer 124. Disposed within conductor 132 is a conventional 9.1K fixed resistor 134, a conventional 2K variable resistor 136 and a conventional single direction diode 138, such as that sold under no. IN4148. A conductor 140 is connected to conductor 132 at a point between variable resistor 136 and diode 138 and runs to connecting point 12 of operational amplifier/buffer 126. A conductor 142 has one end connected to conductor 122, which is connected to connecting point 14 of operational amplifier/buffer 126, and a second end connected to a wiper of a conventional 5K variable resistor 144. Disposed within conductor 142 is a first conventional 100K resistor 146 and a second conventional 100K resistor 148. Variable resistor 144 is disposed with one end running to ground and the other end running to virtual ground circuit 59. Connected to conductor 142 is a conductor 150, which has one end running to connecting point 13 of operational amplifier/buffer 126 and the other end running through a conventional 47K fixed resistor 152 into virtual ground circuit 59.

Figure 7:
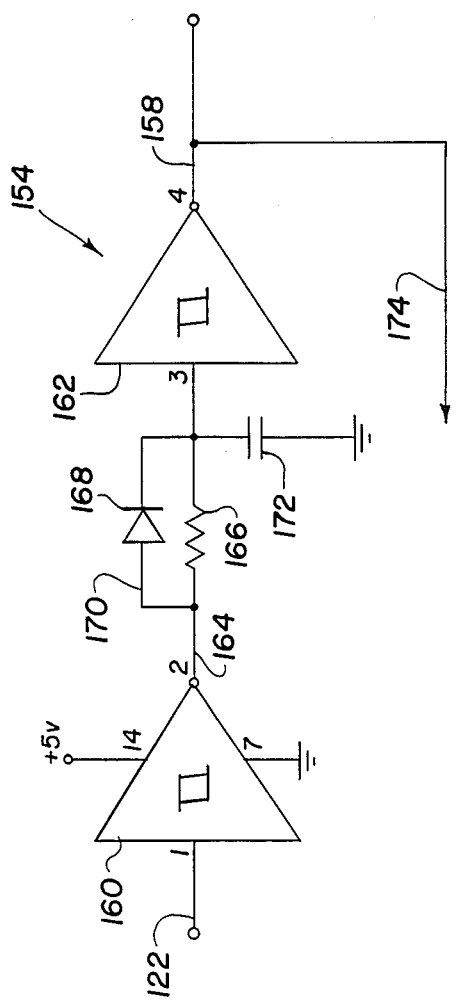
FIG. 7 is a schematic drawing of a portion of the electrical interface circuit shown in FIG. 4.

As best seen in FIGS. 4 and 7, a schmitt trigger threshold detector circuit 154 for providing a pulse signal 156 through conductor 158 in response to the negative going output signal 122 passing through conductor 122 is connected to inverting absolute value amplifier circuit 118 by conductor 122. Schmitt trigger threshold detector circuit 154 includes two hex schmitt triggers 160 and 162, which are of conventional design, such as those sold by National Semiconductor under no. MM74C14, with its connecting points being indicated on the drawing. Hex schmitt trigger 160 is operated off of the +5 volt dc power provided by the mouse port of computer 20 at connecting point 14. Also connected to hex schmitt trigger 160 is conductor 122 to connecting point 1, ground running to connecting point 7 and a conductor 164 to connecting point 2, which runs to connecting point 3 of hex schmitt trigger 162. Disposed within conductor 164 is a conventional 330K fixed resistor 166. A conventional single direction diode 168, such as that sold under no. IN4148, is disposed within a conductor 166, which is connected on each side of resistor 166 to conductor 164. A conventional 0.01 microfarad capacitor 172 is connected to conductor 164 at the junction of conductors 164 and 170 with one plate of capacitor 172 running to ground. A conductor 174 is joined to conductor 158 to carrying a signal to connecting point 11 of switch 70 in sample and hold circuit 66 to regulate the reference signal being provided to differential amplifier circuit 80.

As best seen in FIGS. 4 and 5, a polarity detector circuit 176 for providing a phase control signal through a conductor 178 directly related to the proportional electrical signal provided to inverting absolute value amplifier circuit 118 is connected by conductor 180 to conductor 116 of differential amplifier circuit 80. Disposed in conductor 180 is a first conventional 10K fixed resistor 182 and a second conventional 10K fixed resistor 184. A high gain, internally frequency compensated operational amplifier 186 is included in polarity detector circuit 176. Operational amplifier 186 is of conventional design, such a that sold by National Semiconductor under no. LM324, with its connecting points beng indicated on the drawing. As shown, operational amplifier 186 is connected to conductor 188 at connecting point 9, to conductor 109 at connecting point 10 and to conductor 178 at connecting point 8. Conductor 188 is connected to conductor 180 and virtual ground circuit 59. A conventional 100K fixed resistor 192 is disposed within a conductor 194, which is connected to conductor 178 and conductor 180 at a point between resistors 182 and 184. Conductor 190 is connected to conductor 180 at a point between resistor 184 and the junction of conductors 180 and 194.

Figure 8:
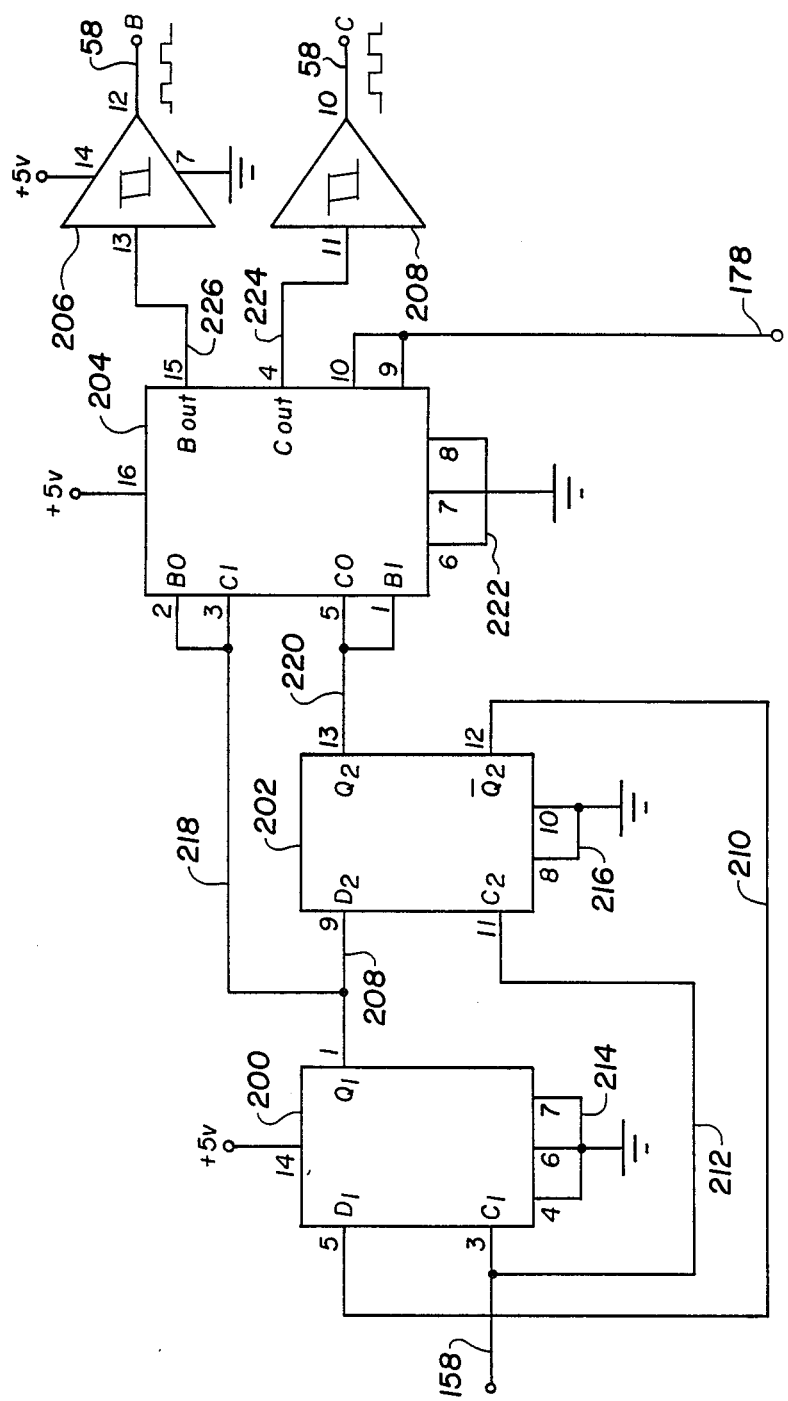
FIG. 8 is a schematic drawing of a portion of the electrical interface circuit shown in FIG. 4.

As best seen in FIGS. 4 and 8, a quadrature converter circuit 196 for providing the pulse output through conductors 58, the pulse output being a pair of square wave electrical signals 198, the square wave electrical signals being 90° out of phase and the phase relationship being determined by the phase control signal, is connected to schmitt trigger threshold detector circuit 154 by conductor 158 and to polarity detector circuit 176 by conductor 178. Quadrature converter circuit 196 includes a first D type flip flop 200, a second D type flip flop 202, a 1-of-2 switch 204, a first hex schmitt trigger 206 and a second hex schmitt trigger 208. Flip flops 200 and 202 are of conventional design, such as that sold in a package by National Semiconductor under the no. 4013, with the package connecting points being indicated on the drawing. A conductor 208 runs from connecting point 1 to connecting point 9 and a conductor 210 runs from connecting point 12 to connecting point 5. Conductor 158 is connected to connecting point 3 and a conductor 212 is connected to conductor 158 and runs to contacting point 11. The +5 volt dc power provided by the mouse port of computer 20 is fed through connecting point 14 into flip flop 200. Connecting points 4, 6 and 7 are connected to one another by a conductor 214, which runs to ground, and connecting points 8 and 10 are connected to one another by a conductor 216, which runs to ground. Switch 204 is of conventional design, such as that sold as a triple 1-of-2 switch package under the no. 4053, with the package connecting point being indicated on the drawing. A conductor 218 connects connecting points 2 and 3 of switch 204 to conductor 208. A conductor 220 connects connecting points 5 and 1 of switch 204 to connecting point 13 of the package of flip flops, which includes flip flop 202. Connecting points 6, 7 and 8 of switch 204 are connected to one another by a conductor 222, which runs to ground. Connecting points 9 and 10 are connected to conductor 178, which runs to polarity detector circuit 176. The +5 volt dc power provided by the mouse port of computer 20 is fed through connecting point 16 into switch 204. Hex schmitt triggers 206 and 208 are of conventional design, such as those sold in a package by National Semiconductor under no. MM74C14, with the package connecting points being indicated on the drawing. A conductor 224 connects connecting point 4 of switch 204 to connecting point 11 of trigger 208 and conductor 226 connects connecting point 15 of switch 204 to connecting point 13 of trigger 206. The +5 volt dc power provided by the mouse port of computer 20 is fed through connecting point 14 into trigger 206. Connecting point 7 of trigger 206 runs to ground while connecting point 12 of trigger 206 and connecting point 10 of trigger 208 are connected to conductor 48.

In operation, a person using computer 20 will insert a first pair of conductors 58 into the mouse port of the computer for moving the cursor in a vertical direction and insert a second pair of conductors 58 into the mouse port of the computer for moving the cursor in a horizontal direction. Computer 20 is activated and head band 26 is secured to the head of the person. The person then raises or nods his head to move the cursor up or down on the screen of computer 20 and moves his head right or left to move the cursor horizontally right or left on the screen. When the cursor is positioned properly on the screen, the person makes a noise into mike 32 to preform the software activities controlling computer 20.

The invention having been described, what is claimed is:

1. Computer control apparatus, comprising: sensing means for converting a mechanical movement into a direct current electrical signal; and electrical interface circuit means connected to said sensing means for converting the direct current electrical signal into a pulse output used in controlling a computer, said electrical interface circuit means including virtual ground circuit means for providing symmetrical plus and minus power from a power source supplied by the computer.

2. Computer control apparatus as set forth in claim 1, further comprising: said sensing means being an inclinometer.

3. Computer control apparatus, comprising: sensing means for converting a mechanical movement into a direct current electrical signal; and electrical interface circuit means connected to said sensing means for converting the direct current electrical signal into a pulse output used in controlling a computer, said sensing means including an inclinometer adapted to convert angular movement relative to gravity into a direct current electrical signal; and means for attaching the inclinometer to a person using the computer so that the angular movement is provided by the person.

4. Computer control apparatus, comprising: sensing means for converting a mechanical movement into a direct current electrical signal; and electrical interface circuit means connected to said sensing means for converting the direct current electrical signal into a pulse output used in controlling a computer, said electrical interface circuit means including sample and hold circuit means connected to said sensor for providing a reference signal; and differential amplifier circuit means connected to said sensing means and to said sample and hold circuit means for providing a proportional electrical signal, the proportional electrical signal being an amplification of the difference in the voltages between the direct current electrical signal and the reference signal.

5. Computer control apparatus as set forth in claim 4, further comprising: said electrical interface circuit means including inverting absolute value amplifier circuit means connected to said differential amplifier circuit means for providing a negative going output signal; and schmitt trigger threshold detector circuit means connected to said inverting absolute value amplifier circuit means for providing a pulse signal in response to the negative going output signal; said sample and hold circuit means connected to said inverting absolute value amplifier circuit means for regulating the reference signal being provided to said differential amplifier circuit means.

6. Computer control apparatus as set forth in claim 5, further comprising: said electrical interface circuit means including polarity detector circuit means connected to said differential amplifier circuit means for providing a phase control signal directly related to the proportional electrical signal provided to said inverting absolute value amplifier circuit means; and quadrature converter means connected to said schmitt trigger threshold detector circuit means and said polarity detector circuit means for providing the pulse output, the pulse output being a pair of square wave electrical signals, the square wave electrical signals being 90° out of phase and the phase relationship being determined by the phase control signal.

7. Computer control apparatus as set forth in claim 6, further comprising: said electrical interface circuit means including virtual ground circuit means for providing symmetrical plus and minus power from a power source supplied by the computer.

8. Computer control apparatus, comprising: an inclinometer adapted to convert angular movement relative to gravity into a direct current electrical signal; means for attaching said inclinometer to the head of a person using the computer so that the angular movement is provided by the person tilting his head; and electrical interface circuit means connecting to said inclinometer for converting the direct current electrical signal into a pulse output used in controlling a computer, said electrical interface circuit means including virtual ground circuit means for providing symmetrical plus and minus power from a power source supplied by the computer, sample and hold circuit means connected to said inclinometer for providing a reference signal, differential amplifier circuit means connected to said inclinometer and to said sample and hold circuit means for providing a proportional electrical signal, the proportional electrical signal being an amplification of the difference in the voltage between the direct current electrical signal and the reference signal, inverting absolute value amplifier circuit means connected to said differential amplifier circuit means for providing a negative going output signal, schmitt trigger threshold detector circuit means connected to said inverting absolute value amplifier circuit means for providing a pulse signal in response to the negative going output signal, said sample and hold circuit means connected to said inverting absolute value amplifier circuit means for regulating the reference signal being provided to said differential amplifier circuit means, polarity detector circuit means connected to said differential amplifier circuit means for providing a phase control signal directly related to the proportional electrical signal provided to said inverting absolute value amplifier circuit means, and quadrature converter means connected to said schmitt trigger threshold detector circuit means and said polarity detector circuit means for providing the pulse output, the pulse output being a pair of square wave electrical signals, the square wave electrical signals being 90° out of phase and the phase relationship being determined by the phase control signal.

9. Computer control apparatus as set forth in claim 1, further comprising: said sensing means being a switch.

10. Computer control apparatus as set forth in claim 1, further comprising: said sensing means being a potentiometer.

11. Computer control apparatus as set forth in claim 1, further comprising: said sensing means being selected from a joystick.

12. Computer control apparatus as set forth in claim 2, further comprising: said sensing means including an opaque body having a chamber; a light source connected to said body to provide light in the chamber; photocell means connected to said body to receive light emitted from said light source for providing an electrical resistance in relation to the amount of light received; and a liquid filter medium supported in the chamber to absorb light emitted from said light source, a sufficient quantity of liquid filter medium being provided in the chamber to prevent light emitted from said light source from impinging upon said photocell means in response to the angular placement of said body relative to gravity.

13. Computer control apparatus as set forth in claim 12, further comprising: said sensing means including said photocell means having first and second photocells connected to said body in an opposed configuration so as to produce a linear output.

14. Computer control apparatus as set forth in claim 12, further comprising: said sensing means including said opaque body having a tube; and said photocell means having first and second photocells connected to said body at opposite ends of the tube so as to provide an opposed configuration to produce a linear output.

15. Computer control apparatus as set forth in claim 12, further comprising: said sensing means including said light source having a light emitting diode having a single peak optical coupling.

16. Computer control apparatus as set forth in claim 15 further comprising: said sensing means including said filter medium chosen to provide vibration dampening and including an oil and a dye supported by the oil, the dye having a color chosen to absorb the single peak optical coupling of the light emitting diode.

17. Computer control apparatus as set forth in claim 3, further comprising: said sensing means including an opaque body having a chamber; a light source connected to said body to provide light in the chamber; photocell means connected to said body to receive light emitted from said light source for providing an electrical resistance in relation to the amount of light received; and a liquid filter medium supported in the chamber to absorb light emitted from said light source, a sufficient quantity of liquid filter medium being provided in the chamber to prevent light emitted from said light source from impinging upon said photocell means in response to the angular placement of said body relative to gravity.

18. Computer control apparatus as set forth in claim 17, further comprising: said sensing means including said photocell means having first and second photocells connected to said body in an opposed configuration so as to produce a linear output.

19. Computer control apparatus as set forth in claim 17, further comprising: said sensing means including said opaque body having a tube; and said photocell means having first and second photocells connected to said body at opposite ends of the tube so as to provide an opposed configuration to produce a linear output.

20. Computer control apparatus as set forth in claim 17, further comprising: said sensing means including said light source having a light emitting diode having a single peak optical coupling.

21. Computer control apparatus as set forth in claim 20, further comprising: said sensing means including said filter medium chosen to provide vibration dampening and including an oil and a dye supported by the oil, the dye having a color chosen to absorb the single peak optical coupling of the light emitting diode.

* * * * *